United States Patent [19]
Latimer

[11] Patent Number: 6,074,874
[45] Date of Patent: Jun. 13, 2000

[54] EPITHELIAL CELL CULTURES FOR IN VITRO TESTING

[75] Inventor: Jean J. Latimer, Pittsburgh, Pa.

[73] Assignee: University of Pittsburgh, Pittsburgh, Pa.

[21] Appl. No.: 08/920,843

[22] Filed: Aug. 29, 1997

[51] Int. Cl.$^7$ .............................. C12N 5/00; C12N 5/02; C12N 5/08
[52] U.S. Cl. ........................ 435/404; 435/371; 435/377; 435/402; 435/408
[58] Field of Search ...................................... 435/404, 405, 435/406, 407, 408, 325

[56] References Cited

U.S. PATENT DOCUMENTS

| | | | |
|---|---|---|---|
| 4,423,145 | 12/1983 | Stampfer et al. | 435/32 |
| 4,829,000 | 5/1989 | Kleinman et al. | 435/240.23 |
| 5,026,637 | 6/1991 | Soule et al. | 435/29 |
| 5,206,165 | 4/1993 | Pauley et al. | 435/240.2 |
| 5,238,840 | 8/1993 | Pauley et al. | 435/240.2 |
| 5,436,152 | 7/1995 | Soule et al. | 435/240.2 |
| 5,670,372 | 9/1997 | Hogan | 435/240.2 |

OTHER PUBLICATIONS

Nuzzolo et al. Tissue Culture Techniques, Warren H. Green, Inc., p. 27, 1983.

GibcoBRL Life Technologies Catalogue and Reference Guide, pp. 3–1 to 3–19, 1993.

Bergstraesser, L., et al., "Stimulation and Inhibition of Human Mammary Epithelial Cell Duct Morphogenesis In Vitro," Proceedings of the Association of American Physicians, 1996, vol. 108, pp. 140–154.

Bergstraesser, L.M. and Weitzman, S.A., "Culture of Normal and Malignant Primary Human Mammary Epithelial Cells in a Physiological Manner Simulates In Vivo Growth Patterns and Allows Discrimination of Cell Type," Cancer Research, Jun. 1, 1993, vol. 53, pp. 2644–2654.

Petersen, O.W., et al., "Interaction with Basement Membrane Serves to Rapidly Distinguish Growth and Differentiation Pattern of Normal and Malignant Human Breast Epithelial Cells," Proc. Natl. Acad. Sci. USA, Oct. 1992, vol. 89, pp. 9064–9068.

Popnikolov, N.K., et al., "In Vivo Growth Stimulation of Collagen Gel Embedded Normal Human and Mouse Primary Mammary Epithelial Cells," Journal of Cellular Physiology, 1995, vol. 163, pp. 51–60.

Stampfer, M.R. and Yaswen, P., "Growth, Differentiation, and Transformation of Human Mammary Epithelial Cells in Culture," in *Mammary Tumorigenesis and Malignant Progression*, 1994, (R. Dickson and M. Lippman, eds.; Kluwer Academic Publishers), pp. 29–48.

Yang, J., et al., "Phenotypic Characterization of Collagen Gel Embedded Primary Human Breast Epithelial Cells in Athymic Nude Mice," Cancer Letters, 1994, vol. 81, pp. 117–127.

*Primary Examiner*—Michael G. Wityshyn
*Assistant Examiner*—Janet M. Kerr
*Attorney, Agent, or Firm*—Foley & Lardner

[57] ABSTRACT

A method and a medium for culturing epithelial cells of both normal and malignant origin is provided. The method entails physically disaggregating tissue samples, placing the resulting fragments onto a surface comprised of basement membrane matrix components, and culturing the tissue in a medium containing preselected fetal and newborn calf sera and rat sera. Both primary explant cell cultures and cell lines, which are long-lived and particularly suitable for further study, are produced. The cultured primary explant cells undergo differentiation to form complex structures resembling those seen in vivo.

5 Claims, 1 Drawing Sheet

EPITHELIAL CELL CULTURES FOR IN VITRO TESTING

FIELD OF THE INVENTION

The present invention relates generally to the field of cytology, and in particular to an improved growth medium and method for culturing epithelial cells. The invention also relates to cultured primary explant cells and cultures of epithelial cell lines.

BACKGROUND OF THE INVENTION

A majority of human cancers arise in epithelial tissue. In the body, epithelial cells separate the internal living stromal tissue from the exterior environment. Epithelial cells exist either as stratified layers that directly face the exterior environment (such as the epidermis) or as a monolayer that can be folded into circular acini or ducts containing lumina.

An epithelial cell is functionally polarized with respect to the two environments it separates. The basal surface of the epithelial is connected to extracellular matrix material which is organized as a basal lamina adjacent to the extracellular matrix of the stromal. The apical surface is free of an apposed extracellular matrix layer, and serves as a boundary to molecular diffusion.

In mammary tissue, the polarity of normal epithelial cells apparently is directed by attachment of the cells to the basal surface. Tumor cells seem to lose this polarity, however. Metastatic epithelial tumor cells secrete hydrolytic enzymes that degrade the basal lamina before they invade the stroma of the breast. Those tumor cells that have degraded the basal lamina lose their polarity, while those cells that remain in contact with non-degraded basal lamina remain polarized.

This difference in morphology between normal and tumor epithelial cells in vivo cannot be reproduced in vitro for several reasons. First, it is very difficult to grow normal epithelial cells in culture at all. Second, because the normal cells grown in culture do not reproduce epithelial morphology observed in vivo, it is difficult to distinguish between normal and transformed cells in culture, although such distinctions are crucial to investigating early events in tumor development. For example, investigations of breast cancer have relied upon the difference in longevity between normal and transformed cells in culture; this difference is the senescence of normal cells and the immortal growth of tumor cells. These in vitro phenomena take time, however, and do not have clear counterparts in vivo.

It would be most useful if epithelium tissue could be grown in vitro conveniently and would exhibit the morphological, physiological, and biochemical behavior characteristic of epithelial cells grown in vivo. These capabilities would allow investigation in vitro of both the development of epithelial cancer, in terms of what triggers such a cancer and how it proceeds, and how better to treat or prevent it.

Because it is difficult to grow normal epithelial cells in culture, most cancer researchers utilize immortal cell lines which are derived from other sources. For example, most studies of breast cancer biology have relied upon a few cell lines which are primarily derived from human breast cancer metastases or rodent primary cells. The best known lines (for example, MCF-7 and MDA-MB231, see Table 1) were generated from metastasized, drug resistant tumors; the lines were established from samples taken from patients who had already undergone radiation therapy and chemotherapy. These tumor lines represent the extreme end of the tumor progression spectrum, and are therefore limited in their usefulness as research tools. In addition to the lack of early stage tumor lines, only one "normal" breast cell line is available (MCF10, see Table 1), and it is not derived from epithelial cells.

TABLE 1

Origin of frequently studied breast tumor cell lines

| Cell Line | Origin (Source) |
| --- | --- |
| MDA-MB231 | Pleural effusion from a 51 yr old Caucasian female with adenocarcinoma of the breast treated with 5-fluorouracil, prednisone, cytoxan, adriamycin, and methotrexate (ATCC, passage 14) |
| BT20 | Infiltrating ductal carcinoma of the breast from a 74 year old Caucasian female (American Type Tissue Culture, ATCC, passage 248) |
| MCF7 | Pleural effusion from a postmenopausal woman with adenocarcinoma of the breast treated with radiation and hormones (ATCC, passage 138) |
| MC7/LY2 | Pleural effusion cells resistant against LY117018 (an estrogenic drug) (ATCC) |
| CAMA-1 | Malignant pleural effusion of a postmenopausal woman with adenocarcinoma of the breast (ATCC, passage 21) |
| SKBR# | Malignant pleural effusion from a 43 year old Caucasian female with adenocarcinoma of the breast treated with radiation, steroids, cytoxan, and 5-fluorouracil |
| MCF10A or F | Myoepithelial cells immortalized with an exogenous agent and derived from normal breast reduction tissue (Michigan Cancer Foundation) |

Primary human normal and tumor-derived breast epithelial cells have only recently been cultured. While both types of cells are difficult to culture, breast carcinomas remain virtually intractable. For example, MDA-MB231 was derived from the 231st attempt to generate a cell line by placing human tumor cells into an immunodeficient mouse strain.

Those cell lines which are available suffer from several disadvantages. The lines represent highly invasive tumor cell types, since most are derived from pleural effusions. They do not represent different stages of tumor growth, as most represent late stage tumors, and they do not represent non-invasive tumor types such as Ductal Carcinoma In Situ ("DCIS"). Furthermore, the lines have undergone many passages. Tumor cells are known for their genomic instability and may further diverge genetically even after establishment of a cell line. Thus, cell lines many generations removed from the original tumors may have undergone selective pressures and clonal evolution. This process can create cell lines that bear little genetic, biochemical, and morphological resemblance to the original tumor from which they are derived. Finally, very little information is available about the original sources of the previously available lines.

Human mammary epithelial cells are typically grown in monolayer culture on tissue culture plastic surfaces in medium containing low concentrations of either serum or pituitary extract. Attempts to grow these cells in a more physiological manner have involved coating the plastic culture surface with either rat tail collagen or a commercially available matrix, MATRIGEL® Matrix.

Conventional methodology for culturing human mammary epithelial involves three steps. The first is to isolate epithelial cells from the tissue sample, primarily by the use of digestive enzymes, resulting in free cells and cell clumps, which can be separated from non-epithelial material. The second step is to place the cells on a surface, which is typically plastic. The third step is to surround the cells with a medium, which typically contains minimal essential nutrients, such as sugars and amino acids, as well as serum (Band, V. and Sager, R (1989) Proc. Nat'l Acad Sci (USA) 86: 1249–1253) or pituitary extract (Hammond, SL, et al. (1984) Proc Nat'l Acad Sci (USA) 81: 5435–5439).

A recent improvement includes coating the culture surface with a material to mimic the extracellular matrix in vivo. The material currently used is rat tail collagen (Yang, J, et al. (1980) J Nat'l Cancer Inst 65: 337–343; Hall, HG, et al. (1982) Proc Nat'l Acad Sci USA 79: 4672–4676) or MATRIGEL® Matrix. Recent reports (Peterson, OW, et al. (1992) Proc Nat'l Acad Sci (USA) 89: 9064–9068; Bergstraesser, LM and Weitzman, SA (1993) Cancer Research 53: 2644–2654) indicate that normal human epithelium, grown on MATRIGEL® Matrix in a complex culture medium which included hormones and growth factors, formed three-dimensional luminal structures called "organoids," while malignant cells remained as single cells and migrated through the MATRIGEL® Matrix. The "organoids" appeared as large structures made of hundreds of cells and many cell layers thick. On the other hand, this system did not form duct-like structures or other structures of increasing complexity. Also, the cultures were not long-lived, surviving for only seven days. These culture methods thus are of limited value for investigating normal epithelial tissue growth and the early events of epithelial tumor development. Such investigations appear to require the existence of viable epithelial stem cells which have the potential to differentiate in vitro into the complex architecture that is normally observed in vivo.

SUMMARY OF THE INVENTION

It is therefore an object of the present invention to provide an improved culture method which is simple and inexpensive, and which results in cultured epithelial tissue that is long-lived and that produces secondary structures that resemble epithelial structures in vivo. As an example, such structures in breast tissue are duct-like, branching and luminal. The culture method includes less stringent and elaborate initial tissue disaggregation techniques, an improved culture medium for use in the initial establishment of the cultures, the presence of extracellular matrix components in the culture chamber, and an optimal density of living cells in the culture chamber. The method can be used to produce primary explant cell cultures, secondary or extended explant cell cultures, or cultures of immortal cell lines from epithelial tissue. The cultures obtained by this method survive for at least 8 weeks, as a primary culture. Alternatively, the cultures may be frozen for subsequent use.

It is a further object of the present invention to provide an enhanced culture medium for use in culturing epithelial tissue. The culture medium contains fetal bovine serum, newborn calf serum, and rat serum. The sera are preferentially pretested to avoid that sera which results in spontaneous differentiation of cultured embryonic stem cells in the presence of LIF, an inhibitor of differentiation, as such sera presumably contain mycotoxins and other impurities. The medium may be further supplemented by providing non-essential amino acids and nucleosides. Further supplements may include growth factors and hormones, preferably estrogen and progesterone. The complexity of the medium induces epithelial attachment to a basal substrate and subsequent differentiation in vitro beyond what has been previously observed.

Yet another object of the present invention is to provide primary explant cell cultures, secondary or extended cell cultures, and cell lines derived from epithelial cells. The cultured primary explant cells produce secondary structures which resemble those in vivo, and are thus morphologically more similar to the organs from which they are derived. Thus, they are a better source of material for conducting studies of early tumorigenesis, for examining the effects of putative carcinogens on normal epithelial cells to determine their role in tumorigenesis, and for investigating the behavior of newly transformed epithelial cells leading to developing better treatments to target these cells. The cell lines are useful for evaluating the effectiveness of various cancer treatments.

The present invention provides an enhanced cell culture medium for culturing human epithelial cells comprising fetal bovine serum, newborn calf serum, and rat serum. The culture medium may be supplemented with non-essential amino acids and with nucleosides. The medium may be further supplemented with growth factors and with hormones.

The present invention further provides a method of culturing excised epithelial tissue, comprising the steps of providing physically disaggregated primary epithelial tissue, placing the disaggregated tissue in a culture chamber on a solid surface of basement membrane matrix components at a final concentration of about 2–50 mg/ml, and culturing the tissue in culture medium comprising fetal bovine serum, newborn calf serum, and rat serum. The initial medium may be removed and replaced with fresh medium.

The present invention further provides a method of producing a cell line derived from epithelial tissue source selected from the group consisting of breast, endometrium, and ovary, wherein the method is as described above, except that the initial culture medium which is removed is placed into a fresh culture chamber, such that the detached cells from the primary explant culture present in the culture medium establish a cell line in the chamber. Alternatively, the present invention provides a method of producing a cell line derived from epithelial tissue source selected from the group consisting of breast, endometrium, and ovary, wherein the method comprises the steps of providing cultured primary explant cells, treating the primary explant culture with trypsin such that free cells arise, and placing the free cells into a fresh culture chamber, such that the detached cells from the treated primary explant culture establish a cell line in the chamber. In both methods, the cultures intermediate to the primary explant culture and the established cell line are considered secondary, or extended, explant cultures.

The invention also provides cultured primary explant cells, cultured extended explant cells, and cultured cell lines that are derived from an epithelial tissue source selected from the group consisting from breast, endometrium or ovary, wherein said cells are produced by the methods described above.

DETAILED DESCRIPTION OF PREFERRED EMBODIMENTS

The present invention contemplates several, related techniques or steps which, when performed together, allow the long-term culture of primary explant cells and of cell lines obtained from normal or malignant epithelial tissue. The first step is preparing epithelial tissue fragments (both normal and malignant) from samples of epithelial tissue. Samples are typically obtained from reduction mammoplasties, lumpectomies, mastectomies, or other surgical techniques. Tissue preparation is accomplished by physically disaggregating the sample by finely mincing it.

The next step is placing the small tissue fragments on a solid surface of basement membrane matrix components; typically, the surface of a plastic or glass culture chamber is coated with a diluted preparation of MATRIGEL® Matrix.

The next step is surrounding the tissue with a complex culture medium, which includes fetal bovine serum, newborn calf serum, and rat serum, and which may be supplemented with non-essential amino acids, with nucleoside, with growth factors, and with hormones. Such medium promotes epithelial cell attachment and differentiation.

The last step is separating individual detached cells from the primary explant culture by removing the initial medium and placing it into fresh culture chambers, such that the detached cells establish a cell line, while new medium replaces that removed from the primary explant cultures. Alternatively, cell lines may be established by treating the primary explant cell cultures with digestive enzymes. This give rise to detached cells, which may be placed into fresh culture chambers, such that the detached cells may then establish a cell line.

The primary explant culture cells are fed by replacing the medium every 24–48 hours. These cultures may be used at any time for morphological, physiological, and biochemical studies. Furthermore, they may be frozen for shipment and subsequent culture and use. The cell lines established from the primary explant cultures remain viable for up to 14 passages or beyond, and also may be used at any time, or frozen for subsequent use.

1. Preparation of Epithelial Fragments

A sample of human tissue collected during surgery should be placed into a simple cell culture medium, such as Dulbecco's Modified Eagle Media ("D-MEM," obtained from Gibco BRL/Life Technologies, Gaithersburg, Md.) supplemented with serum and antibiotics, immediately after surgical dissection to avoid drying and to keep the cells viable. Typically, the medium supplement comprises 10% fetal calf serum and 1× Pen/Strep (which is 100 units/ml of penicillin and 100 ug/ml of streptomycin, obtained from Gibco/BRL). The tissue sample should be refrigerated until it is further processed. It can be refrigerated for up to 5–24 hours, but it is preferable to use it sooner; the less time the tissue is stored refrigerated, the better are the resulting cultures in terms of recovery of cells and plating efficiencies.

Immediately before use, the tissue sample is rinsed in a buffered saline solution supplemented with antibiotic, preferably 1× phosphate buffered saline ("PBS") with 2× antibiotic/antimycotic (which is 200 units of penicillin, 200 $\mu$g/ml streptomycin, and 500 ng/ml amphotericin B, obtained from Gibco/BRL). The tissue sample is then finely minced, preferably with surgical scissors. Other means of mincing the tissue include slicing it with a scalpel, chopping it with a razor blade, or gently forcing it through a mesh screen. The tissue pieces are then immediately partly submerged in pre-warmed complex culture medium, such as Magee-Women's Research Institute-I ("MWRI-I", see Table 2) supplemented with 2× antibiotic/antimycotic, and then moved onto a MATRIGEL® Matrix coated chamber. The tissue is preferably moved by pipetting or by using forceps.

If there is a great deal of fat in the dish, the tissue pieces may be centrifuged after mincing to separate the fat from the tissue; preferably, the sample is centrifuged at 800 rpm for 5 minutes. The fat will float to the top of the liquid where it can be removed. The solid tissue will form a pellet, which may be gently resuspended in MWRI-I. The tissue fragments can then be plated, or placed onto a solid substrate.

The resulting sample from normal human tissue contains fat tissue, stromal or connective tissue, and glandular tissue. The fat tissue consists of fat cells. The connective tissue is mostly acellular with some stromal fibroblasts, which help maintain the collagen or connective tissue. The glandular tissue consists of the epithelial cell structure, comprising epithelial and related cells. In breast tissue, such related cells are myoepithelial cells. Breast epithelial cells in vivo form ducts and lobules where milk is stored; the myoepithelial cells, which form a cell layer surrounding the lobules and ducts, are muscle cells which help squeeze the ducts and lobules to secrete milk.

A sample from normal epithelial tissue probably also contains stem cells, which are pluripotent, or capable of differentiating into a mature cell of at least one mature cell type. Thus, stem cells are embryonic precursor cells, and are present in every organ tissue, even mature organs, where they give rise to mature cells upon demand. Stem cells are found in all layers of epithelial layers, and are especially active in this tissue which must frequently replace worn-out cells.

While not bound by this hypothesis, it appears that the presence of stem cells is necessary for the successful long-term culture of normal epithelial tissue samples. These cells may also be involved in differentiation of the primary explant cultures to more complex structures in vitro. Whereas cell migration may account for some of the formation of domes in culture, differentiation of cultured epithelial tissue from domes to ductal structures which contain lumen probably requires the presence of stem cells. Finally, stem cell viability may be dependent upon a rich culture medium, such as is claimed in the present invention; culture media used previously may not have been suitable for sustained stem cell culture, resulting in the death of these cells.

The resulting sample prepared from human tumor tissue consists predominantly of tumor cells, with some blood tissue present, comprising blood and vascular cells.

The physical disaggregation of the primary tissue is gentle; it does not reduce cells to the single cell level. It appears to retain epithelial cell to cell connections and architecture, and to minimize depolarization of normal apical/basal functioning. The resulting variously sized tissue clumps, which maintain some of the original tissue architecture, may then be placed into culture. Physical disaggregation also avoids the use of digestive enzymes, such as collagenase and trypsin, which can remove the extracellular matrix proteins from the surface of the cells and thus cause disregulation of the cell membrane.

The method for preparing epithelial fragments described above works well for samples obtained from most epithelial tissues. However, minor modifications may be necessary for some sample sources. For example, the method may be used as described for samples obtained from breast and endometrium tissue. In the ovary, by contrast, the epithelium is present as a single-cell layer on the surface of the organ. For samples obtained from the ovary, cells for culture are obtained by mechanically scraping this surface epithelial layer off, and then collecting the cells by centrifuging the sample at low speeds (800 rpm, 5 minutes). The pelleted cells are then gently resuspended as described above, and further treated as described below.

2. Preparation of Solid Substrate

The surfaces of the culture chamber are coated with a solid surface of basement membrane matrix components at a final concentration of about 5–50 mg protein/ml; preferably, the final concentration 13 about 10–20 mg protein/mg. Basement membranes are continuous sheets of specialized extracellular matrix that are found at the base of all lumen-lining epidermal junctions. The basement membranes in vivo provide a structural framework to which cells are anchored, and they play an important role in regulating cell growth, differentiation, and migration.

Preferably, the matrix components are obtained as the commercially available MATRIGEL® Matrix (Collaborative Biomedical Products/Becton Dickinson Labware, Bedford, Mass.). MATRIGEL® Matrix is extracted from the Engelbreth-Holm-Swarm ("EHS") mouse tumor, a tumor rich in basement membrane. The major matrix components are laminen, collagen IV, entactin, and heparin sulfate proteoglycan ("HSPG"). The matrix also contains growth factors, matrix metalloproteinases (collagenases), and other proteinases (plasminogen activators), as well as some as yet undefined extracellular matrix components. At room temperature, MATRIGEL® Matrix gels to form a reconstituted basement membrane. One advantage of MATRIGEL® Matrix is that it encourages epithelial cell attachment and differentiation, and discourages growth of other cell types.

The commercial MATRIGEL® Matrix preparation is diluted with a simple cell culture medium, such as D-MEM, to a final concentration of about 5 to 50 mg/ml. Preferentially, the MATRIGEL® Matrix is diluted about 1:1, to a final concentration of about 10–20 mg/ml. There are several advantages to diluting the MATRIGEL® Matrix. MATRIGEL® Matrix has been shown to select for epithelial cell growth and discourage non-epithelial cell growth. At the commercial concentration, however, MATRIGEL® Matrix is difficult to handle. It is unwieldy, and isolating acinar structures out of an embedded culture, as has been previously reported, is messy and labor intensive, even if the cultures are first treated with a digestive enzyme cocktail such as DISPASE (which is derived from metalloproteases prepared from *Bacillus polymyxa* and obtained from Collaborative Biomedical Products/Becton Dickinson Labware, Bedford, Mass.). In addition, this type of embedded culture is not particularly accessible if the cells are to be examined by microscopic imaging after specific treatments.

Thus, diluting the MATRIGEL® Matrix increases the ability to manipulate the primary explant cell culture samples, which is especially important in microscopic imaging utilized in morphological investigations. Finally, since MATRIGEL® Matrix is expensive, diluting it decreases culture costs. Because MATRIGEL® Matrix provides growth factors as well as the matrix components, the tissue culture medium MWRI-I is not supplemented with growth factors; although it may be supplemented with hormones such as estrogen and progesterone (see Table 2).

3. Culture Medium

A novel culture medium is provided which comprises fetal bovine serum, newborn calf serum, and rat serum. The sera are provided at a concentration of about 2.5% to 40%, 2.5% to 40%, and 1% to 10%, volume to volume, respectively, such that the total concentration of combined sera in the medium is not greater than about 45%. Preferentially, the sera are present at a concentration of about 10%, 10%, and 5%, respectively.

The bovine sera are selected by pretesting the effects of the sera on the growth and differentiation of cultured embryonic stem cells in the presence of LIF, an inhibitor of differentiation; sera which result in spontaneous differentiation of said stem cells are rejected.

The bovine sera are preferentially pre-tested on embryonic stem cells at approximately passage 13. The embryonic stem cells are cultured for 24 hours, which allows them to attach to a gelatin-coated surface. The original culture medium is then replaced with medium containing either older, pre-selected sera or untested sera. The cells are cultured for 3 days, and their morphology observed at 24 hour intervals after the initial medium replacement.

The difference between undifferentiated cells and differentiated cells is dramatic. Undifferentiated embryonic stem cells grow as a smooth sheath or as smooth colonies of cells. Differentiation of these cells during the testing of the media appears as a new layer forming on top of the sheath, or as irregular asymmetric growth of the colonies, or as the formation of a new cell type off of the colonies or sheath. If the embryonic stem cells differentiate spontaneously in the presence of LIF, the serum is rejected since it has components (presumably mycotoxins) that are causing stress and spontaneous differentiation. Several lots of newborn and calf sera which have been selected by this test have proven effective for mammary epithelial cell culture. Other lots which were rejected on the basis of this criterion were not used for mammary epithelial cell culture.

The enhanced culture medium further comprises a simpler cell culture medium which comprises a buffer, inorganic salts, essential amino acids, sugars, vitamins, and preferably at least one indicator dye. Such culture media are well known in the art, and include, for example, various formulations of Dulbecco's Modified Eagle Media ("D-MEM," obtained from Gibco BRL/Life Technologies, Gaithersburg, Md.).

The culture medium may be supplemented with nonessential amino acids, and with nucleosides. The nonessential amino acids may include any of the non-essential amino acids, in any combination; typically, all are present. Each non-essential amino acid is provided in the range of about 10–150 mg/500 ml of the final culture medium. The nucleosides include adenosine, guanosine, cytosine, uridine, and thymidine. Each nucleoside is provided in the range of about 10–200 mg/500 ml of the final culture medium.

The culture medium may further be supplemented with growth factors and with hormones. The growth factors are provided at about physiological concentrations. The hormones are preferably estrogen and progesterone, provided at about physiological concentrations.

Finally, the culture medium is preferably supplemented with reducing agents and with antibiotics. The reducing agents include B-mercaptoethanol, and are preferably provided at about 0.002%–0.009%, and most preferably at about 0.007%. The antibiotics are preferably broad-spectrum antibiotics, and may include penicillin, streptomycin and amphotericin B; antibiotics are preferably provided in the range of about 50–500 units/ml or 0.5–500 ug/ml.

A preferred embodiment of the culture medium, MWRI-I, is detailed below in Table 2.

TABLE 2

MWRI-I Medium
(Shelf life is 10 days)

| COMPONENTS | |
|---|---|
| 5 ml | nonessential amino acids stock (Gibco BRL/Life Technologies, Gaithersburg, MD) |
| 5 ml | β-mercaptoethanol stock (see below) |
| 5 ml | nucleosides stock (see below) |
| 5 ml | 100x Pen-strep (Gibco) |

TABLE 2-continued

MWRI-I Medium
(Shelf life is 10 days)

| COMPONENTS | |
|---|---|
| | 10,000 units/ml penicillin |
| | 10,000 ug/ml streptomycin |
| | optional: a higher concentration of up to 2–3X final concentration may be used during the first few days of primary culture, and then reduced |
| 12.5–200 (pref, 50) ml | bovine serum, heat-inactivated (Hyclone, Logan, UT) |
| 12.5–200 (pref 50) ml | newborn calf serum, heat-inactivated (Sigma, St. Louis, MO) |
| 5–50 (pref 25) ml | rat serum, heat-inactivated and immediately centrifuged (Harlan Sci., Indianapolis, IN) |

The combination listed above is made up to 500 ml with D-MEM.

β-mercaptoethanol Stock (make fresh weekly)

$\mu$l β-mercaptoethanol (Sigma) in 10 ml sterile PBS (do not filter sterilize, as it will dissolve the cellulose nitrate filter); store at 4° C. for up to one week Nucleosides Stock (make fresh every three months)

To prepare 100 ml:

80 mg Adenosine (Sigma, St. Louis, Mo.)
85 mg Guanosine (Sigma)
73 mg Cytosine (Sigma)
73 mg Uridine (Sigma)
24 mg Thymidine (Sigma)

Add the components listed above to 100 ml distilled water and dissolve by warming to 37° C. Filter sterilize and aliquot while warm. Store at 4° C. Warm before each use.

4. Establishment of Primary Explant Cultures, Secondary or Extended Cultures, and Cell Lines The disaggregated epithelial tissue fragments are placed onto the solid surface of basement membrane matrix components prepared as described. Preferably, the tissue is pipetted into a culture chamber, the surface of which is coated with MATRIGEL® Matrix, diluted 1:1 as described above, and prewarmed to 37° C.

The culture chamber should be the smallest size chamber that is feasible for use in subsequent experiments. Preferably, such culture chambers are about 2 cm long by 2 cm wide by 1 cm high. Examples of preferred chambers include 2 well chamber slides, which are 2 chambers mounted on a glass slide and covered with a lid (obtained from Nunc Inc., Naperville, Ill.), and cell-well dishes, which are clusters of 6, 12, or 24 flat, rounded cells covered with a lid (obtained from Corning Glassworks, Corning, N.Y.). It is preferable to crowd the tissue; thus, as much tissue as possible should be placed in each chamber. This generally results in about 0.25–0.5 g tissue/chamber, although less tissue can be used if necessary or desirable for other reasons.

The minimum volume of cell culture medium, preferably MWRI-I, should be used such that the tissue fragments have direct contact with the basement membrane matrix on the bottom of the culture chamber. Such direct contact should be maintained for a few days, and preferably for 24–48 hours.

The tissue is incubated at 37° C. To avoid evaporation of the small amount of medium in small culture chambers in the incubator, a closed container containing Whatman paper saturated with distilled water should be placed around the culture chamber.

To establish primary explant cell cultures, the medium should be changed every 24 hours for the first 4 days. The cultures should be maintained initially in a crowded state with densely packed cells and tissue pieces.

Microscopic domes will be visible on normal mammary epithelial tissue after 24–48 hours. "Dome" refers to the morphology of mammary tissue when the cells grow in aggregates that look like rounded colonies. After the formation of domes, ductal structures will be visible after 5–7 days. These structures will increase in complexity for up to 8 weeks.

Secondary, or extended, explant cultures may be established by one of two procedures. In the first procedure, the medium which is removed from the primary explant culture after the first day of culture is placed into fresh culture chambers, and the detached isolated cells present in the medium allowed to establish a secondary culture. Alternatively, the primary explant cultures may be disaggregated by enzymatic digestion, giving rise to detached and free living cells that can be seeded into a new chamber and used to generate a secondary culture. Several enzymes are suitable for the enzymatic digestion step; one example is the use of trypsin at 0.25% (obtained from Gibco BRL/Life Technologies, Gaithersburg, Md.) under well-known conditions. (Freshney, R.I. (1994) *Culture of Animal Cells*, 3rd Edition (Ed: Freshney, R.I.; Willey-Liss, Glasgow)).

The secondary explant cells are cultured in sterile plastic tissue culture flasks in an appropriate medium; preferably, this medium is D-MEM, with about 10% fetal calf serum. The surface of the plastic tissue culture flask may be initially coated with gelatin; the cells then grow on top of the gelatin. The cells are grown until the desired density is reached; usually, this is when the surface area is completely covered with cells (known as a confluent layer of cells). The cells are then first gently treated with digestive enzymes to separate the cells; preferably, about 0.25% trypsin with about 1 mM EDTA is used, and the process is monitored microscopically to determine when the cells begin to separate. At that point, the cells are then diluted with medium and placed, or plated or seeded, into new culture flasks. Each step of separating the cells and placing them into a new flask is known as a passage.

The size of the culture flasks may vary from about 12 cm$^2$ to about 75 cm$^2$. Usually, the cells are taken in incremental steps to larger and larger surface areas. In addition, the cultures may be weaned onto a more defined, less complex medium by passing them into medium of decreasing richness with each successive passage.

Cell lines may be established from the secondary explant cultures by continuing to passage the cells 14 times or more.

Figure 1:
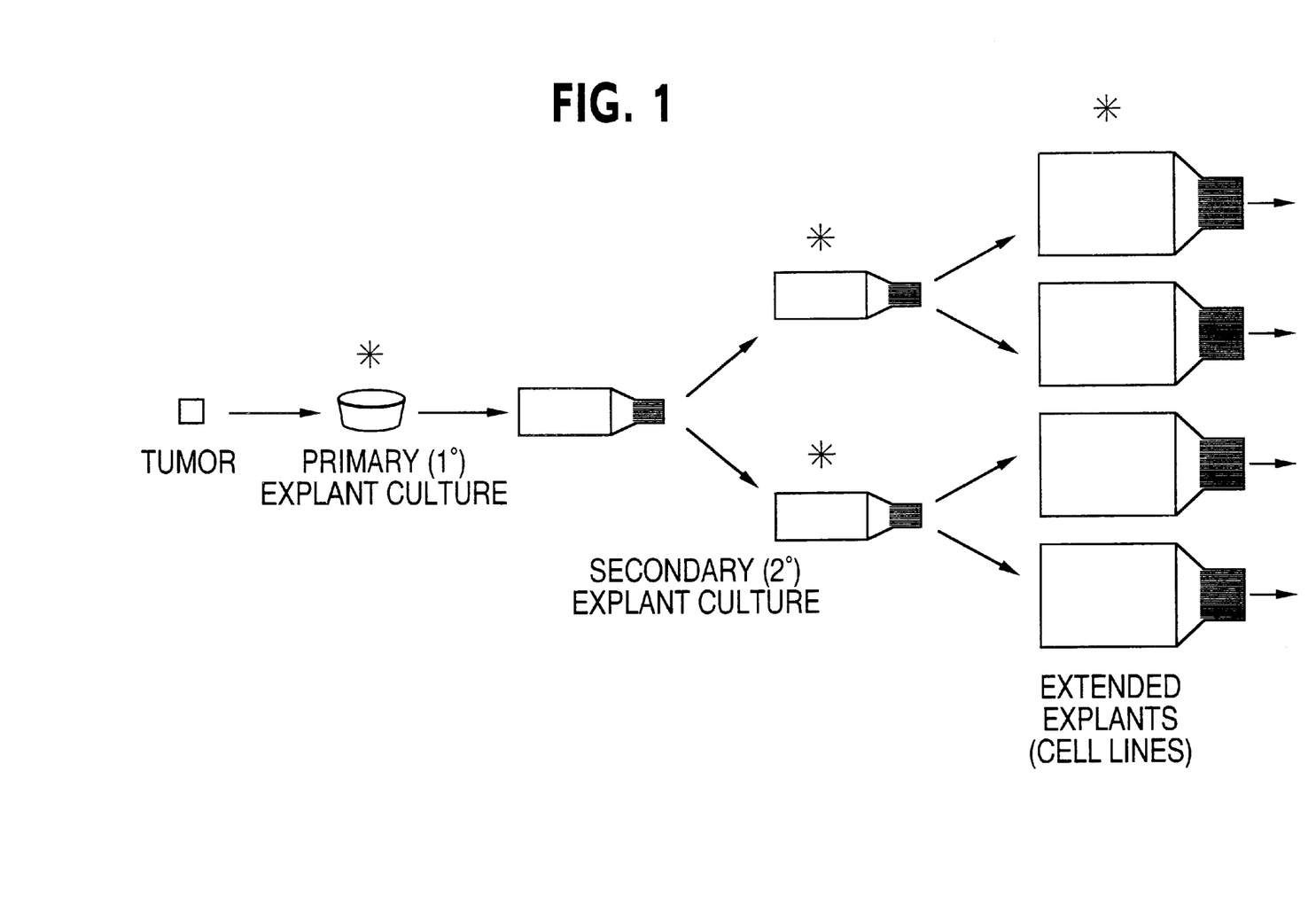
FIG. 1 is an diagrammatic illustration of how primary explant cell cultures, secondary or extended cell cultures, and cell lines cells are generated from epithelial tissue.

Thus, the preceding methods allow the establishment of three different types of cultures; these cultures are illustrated diagrammatically in FIG. 1. The first culture is the primary explant culture, which is the culture of the original epithelial tissue sample. This culture typically remains in the original culture chamber, and survives up to about 8 weeks. The culture of normal epithelial tissue generally develops the morphology observed in vivo, to the extent of forming ductal structures which have lumina.

The second type of culture is the secondary, or extended, explant culture, which is derived from the primary explant culture as described above. This culture is defined as those cells which undergo at least one but less than 14 passages. It represents only those cell types which can adapt to tissue culture. The secondary explant culture is particularly useful for generating large amounts of cultured tissue. In addition, it is an intermediate in the establishment of cell lines, which are the third type of cell culture.

A cell line is defined as those cultured cells which have undergone 14 or more passages. Cell lines represent those cells which are immortal; typically, only 10% to 20% of cells present in the secondary explant culture become immortal.

Passaging is defined as moving cultured cells from one culture chamber to another. It is the means by which cultured cells are propagated to the subsequent generation.

Any of the resulting cell cultures may then be characterized by two different procedures, although secondary or extended explant cultures and cell lines are most typically analyzed by these procedures. These characterizations are traditional measures of the cloning efficiency and of the tumorigenicity of the cultured cells, using well-known techniques.

The first procedure is used to evaluate the cloning efficiency of the cultured cells by determining cell growth on methyl cellulose, which is a soft agar. The procedure allows a determination of anchorage-independence, a cell culture characteristic associated with transformation and immortalization.

The second procedure is used to evaluate the tumorigenicity of the cultured cells by determining tumor formation from cells injected into suitable hosts. Typically, samples of the cultured cells are injected into Nude or Severely Compromised Immunodeficient ("SCID") mice; the degree of tumorigenicity is determined by injecting mice with increasing number of cells. If secondary explant cultures are evaluated, cell lines can be established from those cells which are proven to be tumorigenic.

5. Utilization of Primary Explant Cell Cultures

The cultured primary explant cells produced by the method of the present method are particularly useful to study the cytotoxic, carcinogenic, and general physiological effects of various agents on epithelial cells. They also are suitable as sources of tissue for investigating in vitro the behavior of newly transformed epithelial cells, in order to develop better treatments to target these cells.

a. Assay of Xenoestrogenic Chemicals

Breast cancer is the second largest killer of women in this country (and the first in women over the age of 60). 186,000 women are diagnosed with breast cancer every year in the USA alone. Breast cancer is on the rise in every industrialized nation in the world except Japan. This apparent rise may be partly a result of the cumulative effects of chemicals in the environment (pesticides and fertilizers) which are stored in fat after ingestion. These chemicals, called xenoestrogens, inappropriately stimulate the luminal epithelial cells of the breasts and have been shown in rats to cause mammary cancer. These chemicals may also be involved in other epithelial cancers, especially those in the endometrium and in the ovary.

The cultured primary explant cells may be used to test the effects of xenoestrogenic chemicals (or other types of putative cancer causing chemicals) on normal human epithelial cells in order to determine whether they cause transformation. The primary explant cell cultures of the claimed invention are an improvement over what has been available previously, as most results have been obtained from rodent model systems and are therefore limited in terms of their relevance to the human in vivo situation.

b. Assay of Estrogen Effects

Although estrogen has been hypothesized to play a role in cancer etiology, this contention is controversial. Cultured primary explant cells from normal epithelium can be used to examine the role of estrogen in tumorigenesis.

c. Assay Procedures

The effect of chemicals on epithelial cells may be tested on either primary explant cell cultures or cell lines, but preferably on primary explant cell cultures. The cultured cells are brought into contact with the test substrate at the desired concentrations for the desired periods of time, and the effects of the substrate on the cells evaluated. Such evaluation may include analysis of biochemical, physiological, genetic, or morphological characteristics.

Such testing, but especially short-term testing, may require a solid surface of basement matrix components which are free of growth factors. In this case, the rich growth medium is removed and replaced by a defined medium which contains the test substrate of interest. Replacement of the rich growth medium with a defined medium also allows evaluation of various factors or treatments which are under consideration as either inducing tumorigenesis, preventing it, or treating it.

d. Experimental Controls

Cultured primary explant cells from normal breast epithelium can be used to provide a relatively "normal" experimental control for studies that have historically utilized transformed cell lines such as MCF 7 and MDA MB231 for molecular analysis of breast cancer cells.

The MCF7 (human breast tumor) line is the most widely used cell line. Other breast tumor cell lines have been used recently as well. However, as noted previously, these cell lines are very late passage numbers (in many cases, the passage number is not known, but it is certainly very large). In addition, they do not represent different stages of tumors, as they are predominantly highly invasive tumor cell types (in fact, most are derived from samples obtained from pleural effusions).

e. Model Systems

Cultured primary explant cells from normal epithelium can be used to characterize the behavior of newly transformed epithelial cells and to develop better treatments to target these cells.

For example, the study of in vitro cell behavior may be investigated by time lapsed videography. Results obtained for cultured cells obtained from breast epithelia have shown that tumor cells are more mobile than normal cells, which form stable three-dimensional structures as described previously. This may allow a determination of what happens initially as cells become tumorous, and what factors trigger this transition.

6. Utilization of Secondary Explant Cell Cultures and Cell Lines

The secondary explant cell cultures and cell lines produced by the method of the present method are also useful for several types of analyses. Because these cultures generate large numbers of cells, they are particularly suited for assays which require a large amount of tissue or a large number of cells.

Thus, these cultures may be used in toxicology testing of various chemicals (such as pesticides, fertilizers, and drugs), to determine whether these chemicals cause tumorigenesis in vitro. They may also be used in chemoprevention studies, as for example in evaluating the effects of a chemical purported to prevent tumorigenesis in the presence of a tumorigenic chemical; the cells are examined for transformation by a resulting malignant morphology.

The cell lines may also be used to examine chemotherapy drug resistance testing in vitro, and for cell behavior studies, such as changes which occur upon metastasis. They are very useful for basic and translational research in the area of molecular genetics, as for example in studies involving samples obtained from patients of very different ages. They are also very useful for investigations of genetic and sporadic origins of tumorigenesis.

Furthermore, the cells which may be grown in tumor bearing mice are also useful in several ways. For example, the cells grown in mice can be used for chemotherapy drug testing in vivo. The cells may also be used in chemoprevention studies (as for example, when cell lines with known tumorigenic capacity are injected into test mice along with chemopreventive chemicals; the assay is the effects on tumor formation in vivo), and in studies of metastasis in vivo (for example, when cultured cells are injected into mice mammary fat pads).

Finally, the method of the claimed invention allows the establishment of cell lines from tumors of different stages, including stage 0 preinvasive breast cancer, known as Ductal or Lobular Carcinoma In Situ, (or "DCIS" or "LCIS"). Although this stage of cancer has been found in many women, it has been estimated that 50–70% of these cases will not progress to invasive carcinomas. However, because there is currently no means to determine which DCIS tumors will become invasive, treatment is suggested for all cases. Cell lines derived from DCIS tumors can provide a valuable diagnostic tool to distinguish between those tumors which will become invasive, and those which will not. Analyses of the cell lines include time lapsed videography to observe morphological behavior of the cells in culture.

EXAMPLE I

Cultured Primary Explant Cells

A. Sample Source

Samples of breast epithelial tumor tissue were obtained from patients who were recently diagnosed with primary breast tumor and who had not yet received any chemotherapy, radiotherapy or tamoxifen. Control tissues were obtained from patients who underwent breast reduction mammoplasty. Cultures were established from tumor tissue and the adjacent "non-tumor" tissues obtained from breast cancer patients, and from normal epithelial tissue obtained from breast reduction mammoplasty patients.

B. Establishment of Primary Explant Cell Cultures from Tumors, Adjacent Epithelium and Breast Reductions The methods outlined above were employed to obtain primary explant cultures from breast epithelial tissues. The epithelial tissues were gently minced with surgical scissors, and placed into culture chambers consisting of MATRIGEL® Matrix coated chamber slides, with the MATRIGEL® Matrix diluted 1:1, volume to volume, as described previously; the samples were then cultured in MWRI-I medium.

Epithelial cells grew off the tissue pieces and became epithelial domes. "Dome" is the descriptive term for the morphology of mammary tissue; that is, the cells grow in aggregates that look like rounded colonies. It was noted that the samples obtained from early stage tumors tended to grow more asymmetrically out of the domes than did the adjacent epithelial, "non-tumor" tissue. Samples obtained from stage 3 tumor cells did not form domes at all, but remained as single cells.

Numerous sets of samples of matched pairs of tumor and adjacent epithelium, as well as samples from several breast reduction mammoplasties, were processed and placed into the culture system of the invention within a few hours after surgery. Overall, 80% of the tumor samples and 70% of the normal epithelial samples, obtained from epithelial tissue adjacent to the tumors and from the breast reduction tissue, attached to the substrate and grew adequately for subsequent Nuclear Excision Repair ("NER") analysis.

C. Immunohistochemical Verification of Mammary Epithelial Cells in Primary Explant Cell Cultures It was possible that multiple cell types would grow in primary explant cell cultures since the breast is primarily a network of interconnecting lobules and ducts made up of different cell types. The ducts are lined with polarized ductal and lobular epithelial cells surrounded by myoepithelial cells which aid in milk secretion by contracting around the ducts. The ductal and lobular epithelial cells are the origin of most breast tumors, although tumors can arise from myoepithelial cells as well. The epithelial cells are the major cells present in the cultured primary explant cells as confirmed by Epithelial Membrane Antigen ("EMA") staining, E29 (DAKO).

EMA labels a variety of normal and neoplastic cells of epithelial origin. This antibody reacts most strongly with mammary epithelia, especially in the apical portion of duct-lining cells. The reaction stains epithelial cell cytoplasm dark brown; nuclei were counter-stained with hematoxylin. Breast myoepithelium does not cross-react with EMA antibodies, nor do stromal fibroblasts. The efficacy of EMA staining for the cultured cells of the invention was demonstrated through the use of several controls.

A section from a paraffin embedded normal breast tissue block was used as a positive control; the results show that EMA stained the mammary epithelial cells lining the lumen of the ducts dark brown, and failed to stain the myoepithelium around the epithelial cells.

The human hepatocarcinoma cell line, Hep 3B, was used as a negative control, since it was not derived from epithelial cells. The HEP 3B cells did not cross-react with the EMA antibody. The MCF-7 cell line was used as a positive control, as it was derived from a human mammary epithelial tumor. The MCF-7 cells treated with the secondary antibody showed no staining, while MCF-7 cells treated with both the primary and secondary antibodies reacted positively with dark brown cytoplasm.

The cultured primary explant cells from a breast tumor and its adjacent epithelial tissue also stained positively as brown cytoplasm, indicating that the growth of mammary epithelial cells was achieved by the tissue culture method of the invention. Only limited amounts of breast epithelial tissue is available for research purposes; tissue samples for EMA staining therefore were available only when sufficient tissue was obtained from pathology to culture a third sample of tumor and adjacent tissue (two samples were used for analysis of DNA repair). Enough tissue was obtained to stain about 30% of all tumor and non-tumor adjacent explants (and 40% of the breast reduction explants) with EMA. Since the results of these EMA antibody reactions consistently showed that the cells growing in primary explant cell cultures were epithelial (with the exceptions noted below), staining with EMA was not performed on every subsequent culture.

Although most of the cultured cells are epithelial, some non-epithelial cells were present in low numbers. These include lymphocytes and fibroblastic cells. The cultured epithelial cells are easily distinguished from the minor presence of these non-epithelial cells on the basis cell size and shape and nuclear morphology.

Epithelial cells were rounded and present in dome-like architecture or cobblestone conformation. "Cobblestone" refers to a rounded conformation which is slightly crushed and irregular, due to crowding of cells. On the other hand, the lymphocytes appeared as much smaller rounded cells, and the fibroblastic cells appeared as larger single cells growing in monolayers. These morphological distinctions were verified by EMA staining. EMA staining also distinguished some cells which are morphologically fibroblastic in cultures obtained from normal breast reduction mammoplasty epithelium.

The fibroblastic cells do not inhibit or disrupt the epithelial structures. In fact, their presence may help to condition the medium and may provide factors which enhance and maintain epithelial cell differentiation. The numbers and distribution of fibroblastic cells vary with each normal breast sample and with the length of time in culture (they may be present from about 20% to less than 50% of the living cells in culture). The fibroblastic cells may grow while remaining tightly attached to the bottom of the dish; the epithelial cells grow to form ducts, both ends of which are attached to the dish, while the central portion is suspended over the fibroblastic monolayer.

D. Comparison of Normal With Tumor Epithelial Cell Behavior by Time-lapsed Videography The in vitro behaviors of normal and tumor primary explant cell cultures were examined by time lapsed videography using a multimode inverted microscope and by Differential Interference Contrast Microscopy ("DIC"). Normal breast epithelial tissue in the culture system of the invention gives rise to stable domes and then progresses to form tubular or ductal structures. Tumor explants in this system do not form tubules or complex structures although some (but not the majority) form domes initially. The cells of these tumor-derived domes flatten and disperse over time and do not remain stable or increase in complexity like those derived from normal epithelial cultures. Cells obtained from stage III tumors did not form domes at all, but remained as single fibroblastic-like mobile cells which repelled each other when cell-to-cell contact occurred.

E. Morphological Characterization by Microscopy

Both domes and more complex tubular epithelial structures were seen in cultured epithelial cells under bright field, differential interference contrast microscopy and Scanning Electron Microscopy ("SEM"). These structures were further examined microscopically.

The existence of lumen within the cultured ducts and some of the domes and ducts by was confirmed by Hoecht Dye Imaging (Optical Sectioning). Optical sectioning of the complex cultured epithelial structures was achieved by a combination of DIC and epifluorescence, utilizing a multimode inverted microscope. The results showed that most of the domes from normal mammary cultures were not hollow and that all of the tubular structures were. The lumen of the tubular structures often may be observed with DIC optics alone.

The use of SEM confirmed that tight junctions exist on the uppermost apical surface of the cultured epithelial cell structures. In vivo, the rim of the apical surface of epithelial cells is connected by tight junctions to adjacent epithelial cells, so that the cell layer serves as a boundary to molecular diffusion. SEM micrographs indicate that the top layer of many of the epithelial domes and also of the more complex tubular structures are joined by tight junctions between the rounded epithelial cells. The flattened appearance and tight ligatures between the cells clearly indicate a close and presumably functional relationship.

The same cultures of breast reduction epithelial tissue examined by SEM were also examined by Transmission Electron Microscopy ("TEM"). The results showed that the cells of the domes are linked by desmosomes, proving that the domes contain epithelial cells. TEM is also used to determine that the internal structure of the endoplasmic reticulum and other organelles of the cells is consistent with polarized functional epithelial cells.

The evidence demonstrates that the complex structures observed in the epithelial tissue cultured by the method of the present invention possess architectural integrity. In addition, these structures are useful components of a model system for studying early events in breast tumorigenesis following chemical or hormonal stimulation or insults.

Although this example deals with breast tissue, similar results are obtained with human ovary and endometrium epithelial tissue cultured by the method of the present invention. Ovarian epithelial cells do not form domes, but the cells are more loosely associated with each other and more easily grow as single cells, relative to cultured cells derived from breast tissue. Endometrium epithelial cells do form domes in culture, but the cultures consist of a more complex mixture of cells than is observed for cultured cells obtained from either breast or ovarian epithelial tissue.

EXAMPLE II

Cultured Cell Lines

The methods outline above were employed to obtain cultured cell lines from breast epithelial tissue. The primary explant cell cultures were established as described under Example I. The cell lines were established by both methods described previously.

Cell lines have been generated from tissue samples obtained from human breast tumors or Ductal Carcinoma In Situ ("DCIS") of patients recently diagnosed with breast cancer (see Table 3). At least forty cell lines were established from 63 tumors, which represents a success rate of more than 60%.

The cell lines represent tumors (which were not subjected to chemotherapy treatment) from stages 0 (or DCIS), I, II, III, and IV. These cell lines provide several advantages over currently available lines. They are the first reported cell lines to be established from DCIS tumors. Furthermore, many of the conventional breast cancer cell lines available from ATCC were derived from drug-resistant pleural effusions (invasive breast tumor cells which had metastasized to the sack around the lung) (Table 1) and are therefore more characteristic of metastatic cells which are resistant to chemotherapy drugs than the primary tumor would be.

Another advantage is the increased information associated with each cell line. This information includes chart information, gathered with Institutional Review Board ("IRB") approval, about the patient and tumor from which each cell line was derived, as well as additional information regarding family history of related types of cancer and other medical chart information. Thus, cells obtained from tumors which are morphologically classified at the same stage and nuclear grade, but which are obtained from patients of very different ages, actually result from different etiological processes. The different cell lines are then of interest or possess different value to different groups of scientists. Those lines established from the tumors of younger patients are of greater interest to geneticists, as the original tumors are more likely to be due to the presence of specific genes. In contrast, those lines established from older patients are of greater interest to scientists conducting environmental testing, as these tumors are more likely due to a response to environmental factors.

Cell lines are usually cloned (diluted to one cell and then expanded as a clonal population from this single cell). This helps to encourage genetic homogeneity, although tumor cells are known to be genetically heterogeneous. Tumor cells are also known for their genomic instability and may further diverge genetically even after cloning. Thus, cell lines many generations removed from the original tumors may have undergone selective pressures and clonal evolution. This process can create cell lines that bear little genetic, biochemical, and morphological resemblance to the original tumor from which they are derived.

Cell lines show no ability to maintain three-dimensional structures in culture; there is no dome formation. Instead, the cells spread out and resemble fibroblasts.

Breast tumor cell lines often are characterized karyotypically, as well as by reference to epithelial membrane and cytokeratin staining. These proteins are associated with specific cell types within the breast and give some idea of the derivation of the cell line. Breast tumors can arise from two of these cell types, the luminal epithelium and the myoepithelium, but most tumors are believed to arise from luminal epithelium.

When the cell lines previously available were analyzed by these methods, only one line retained the ability to be stained with EMA, MCF-7. The remaining non-staining lines include cells derived from "normal" epithelial tissue, such as MCF-10a, which was derived from myoepithelial cells from a benign fibroadenoma tumor (see Table 1).

The cell lines established by the method of the claimed invention are also characterized karyotypically and by immunohistochemical staining, including cytokeratin staining, epithelial membrane staining and desmin staining. This characterization allows a determination of which cell type make up the cell lines.

The cell lines of the claimed invention are capable of vigorous growth, freeze and thaw well, and have in several cases survived "crisis," which is a period of high cell mortality giving rise over time to outgrowth of the cells most adapted to in vitro cell culture. Several of the lines have been extended to over 20 passages.

The criteria for the establishment of a tumor cell line include:

1) Immortalized (unlimited) growth of the cells derived from a tumor, and

2) Growth
   a) in an immuno-compromised mouse strain such as Nude mice or SCID mice, OR
   b) in soft agar or methylcellulose.

Verification that the cell lines consist of tumor cells is accomplished by either of two means. The first approach involves transplanting the cells subcutaneously or into the abdominal or mammary fat pads of SCID or Nude mice; the development of tumors in vivo indicates that the lines are capable of tumorigenic growth in animal hosts. Another classical approach for establishing that cell lines are immortalized cell lines entails growing the cells in soft agar. Fourteen lines, representing different stages of breast cancer, were chosen for initial testing. The different stages include normal, stages 0 or DCIS, I, II, III, and IV, and lymph node metastases.

TABLE 3

Cell Lines Derived from Breast Tumors

Cell lines were derived from Breast Reduction Line (BRL), Breast Tumor Line (BTL), preinvasive breast cancers or Ductal Carcinoma In Situ (DCIS) or Lymph Node Metastasis from a breast tumor (LNTL—Lymph Node Tumor Line). An asterisk (*) indicates that these 2 cell lines came from the same patient (one represents the primary tumor and the other represents the secondary metastasis).

| Cell line # | Breast Cancer | Age | Stage | Nucl. Grade | Size (cm) | ER/PR | LN Status (# pos) | Passage Froz. Down |
|---|---|---|---|---|---|---|---|---|
| JL BRL 1 | Breast Reduction | 35 | | | | | | P5, 9 vials |
| JL BRL2 | Breast Reduction | 19 | | | | | | P6, 9 vials |
| JL BRL3 | Breast Reduction | 21 | | | | | | P4, 3 vials |
| JL BRL4 | Breast Reduction | 55 | | | | | | P4, 3 vials |
| JL BRL5 | Breast Reduction | 26 | | | | | | P4, 6 vials |
| JL DCIS-1 (JL BTL 18) | DCIS | 36 | 0 | | | | | P3, 3 vials |
| JL DCIS 2 (JL BTL 24) | DCIS | 47 | 0 | | 3.5 | | | P5, 9 vials |
| JL DCIS 3 | DCIS | 39 | 0 | | | | | P5, 9 vials |
| JLK 1 | Ductal | 24 | 2B | 2 | 2.2 | − | LN+ | P4, 2 vials |
| JL BTL 1 | Ductal | 81 | 3B | 3 | 5 | −/− | 7/12 | P4, 2 vials |
| JL BTL 2 | Ductal | 59 | 2B | 3 | 2.5 | +/+ | 2/13 | P4, 2 vials |
| JL BTL 3 | Ductal | 54 | 2B | 3 | 2.3 | +/+ | 5/19 | P4, 2 vials |
| JL BTL 4 | Ductal | 34 | 1 | 3 | 1.5 | −/+ | 2/9 | P3, 2 vials |
| JL BTL 5 | Ductal | 62 | 2B | 3 | 1.7 | −/− | | P3, 2 vials |
| JL BTL 6 | Ductal | 56 | 3 | 3 | 4.7 | | 5/23 | P6, 4 vials |
| JL BTL 7 | Ductal | 31 | 2 | 3 | 2.6 | −/− | 0/15 | 9 vials |
| JL BTL 8 | Ductal | 52 | 1 | 2 | 2 | +/+ | 0/20 | P5, 3 vials |
| JL BTL 9 | Ductal | 46 | 2A | 2 | 2.5 | +/+ | 0/25 | P5, 9 |

-continued

| Cell line # | Breast Cancer | Age | Stage | Nucl. Grade | Size (cm) | ER/PR | LN Status # pos) | Passage Froz. Down |
|---|---|---|---|---|---|---|---|---|
| JL BTL 10 | Ductal | 38 | 2B | 3 | 2.6 | −/− | 3/23 | P5, 9 vials |
| JL BTL 11 | Lobular | 66 | 2A | 1 | 2.6 | +/− | 0/18 | P5, 9 vials |
| JL BTL 12 | Ductal | 37 | 3A | 3 | 3 | +/+ | 8/16 | P5, 9 vials |
| JL BTL 13 | Ductal | 61 | 2B | 3 | 3 | −/− | 3/18 | P6, 6 vials |
| JL BTL 14 | Ductal | 53 | 1 multif | 3 | 1.5 | +/+ | 0/17 | P4, 6 vials |
| JL BTL 15 | Ductal | 60 | 2A | 3 | 2.6 | −/− | 0/17 | P5, 3 vials |
| JL BTL 16 | Ductal | 36 | 2 | 2 | 2.5 | | 1/16 | P4, 3 vials |
| JL BTL 17 | Ductal | 69 | 3 | 3 | 3.8 | +/+ | 7/20 | P2, 4 vials |
| JL BTL 19 | Ductal | 44 | 1 multif | 3 | 1.2 | | ND | P3, 3 vials |
| JL BTL 20 | Ductal | 62 | 4 | 2 | 4 | | | 9 vials |
| JL BTL 21 | Ductal | 46 | 4 | 2 | 3.2 | +/+ | L21/23 | P5, 9 vials |
| JL BTL 22 | Ductal | 68 | 1 | 3 | 1.3 | | | P5, 9 vials |
| JL BTL 23 | Ductal | 78 | 2 | 3 | 2.1 | | 35/39 | P5, 9 vials |
| JL BTL 25 | Lobular | 40 | 2 multif | 2 | 3.7 | | 0/19 | P5, 9 vials |
| JL BTL 26 | Ductal | 29 | 2 | 3 | 2.1 | | 0/19 | P5, 9 vials |
| JL BTL 27 | Ductal | 52 | 2 multif | 3 | 3.2 | | 0/12 | P5, 9 vials |
| JL BTL 28 | Medullar | 72 | 2 | 3 | 2.5 | −/− | 0/11 | P5, 9 vials |
| JL BTL 29 | Mucin. | 39 | 2 | 2 | 2.5 | | 0/22 | P5, 7 vials |
| JL BTL 30 | Ductal | 39 | 2 | 3 | 3.1 | | 1/13 | P5, 5 vials |
| JL BTL 31 | Ductal | 65 | 2 | 3 | 2.4 | | 0/23 | P5, 9 vials |
| JL BTL 32 | Ductal | 38 | 1 | 3 | 1.2 | −/+ | 0/19 | P5, 6 vials |
| JL LNTL 2 | LN met | 48 | | | | | | P4, 6 vials |
| JL LNTL 3 | LN met | 78 | | | | | | P4, 9 vials |
| JL LNTL 1* | LN met. | 37 | 3A | 3 | 3 | +/+ | 8/16 | P5, 9 vials |

It is understood that this invention is not confined to the particular embodiments herein illustrated and described, but embraces such modified forms thereof as come within the scope of the following claims.

What is claimed is:

1. A cell culture medium comprising about 2.5% to about 40% by concentration fetal bovine serum, about 2.5% to about 40% by concentration newborn calf serum, and about 1% to about 10% by concentration rat serum, such that the total concentration of sera is no greater than about 45%, wherein (A) said fetal bovine serum and said newborn calf serum are selected by pretesting the effects of the sera on the growth and differentiation of cultured embryonic stem cells in the presence of LIF, such that sera that cause spontaneous differentiation of said cultured embryonic stem cells are rejected, and (B) epithelial cells cultured in said cell culture medium form secondary structures which morphologically resemble those in the organs from which said epithelial cells are obtained.

2. The cell culture medium of claim 1, wherein said fetal bovine serum is provided at a concentration of about 10%, said newborn calf serum is provided at a concentration of about 10%, and said rat serum is provided at a concentration of about 5%.

3. The cell culture medium of claim 1, wherein the cell culture medium overlays a solid surface, wherein the solid surface comprises basement membrane matrix components in a concentration of about 2–50 mg/ml.

4. The cell culture medium of claim 3, wherein said concentration of basement membrane matrix components is 10–20 mg/ml.

5. The cell culture medium of claim 3, wherein the matrix components comprise proteins which are extracted from the Engelbreth-Holm-Swarm (EHS) mouse tumor.

* * * * *